United States Patent [19]

Walzel et al.

[11] Patent Number: 4,813,287
[45] Date of Patent: Mar. 21, 1989

[54] TESTING DEVICE FOR DETERMINING MECHANICAL PROPERTIES OF A GRANULATED MATERIAL

[75] Inventors: Peter Walzel, Dormagen; Richard Juffa, Cologne, both of Fed. Rep. of Germany

[73] Assignee: Bayer Aktiegesellschaft, Fed. Rep. of Germany

[21] Appl. No.: 111,712

[22] Filed: Oct. 23, 1987

[30] Foreign Application Priority Data

Nov. 3, 1986 [DE] Fed. Rep. of Germany ... 8629187[U]

[51] Int. Cl.⁴ ............................................. G01N 3/08
[52] U.S. Cl. ......................................... 73/835; 73/81
[58] Field of Search ................. 73/818, 819, 821, 851, 73/81, 835

[56] References Cited

U.S. PATENT DOCUMENTS

| 2,670,624 | 3/1954 | Faris, Jr. et al. | 73/851 X |
| 4,393,717 | 7/1983 | Mason et al. | 73/821 |

Primary Examiner—Jerry W. Myracle
Attorney, Agent, or Firm—Connolly and Hutz

[57] ABSTRACT

For improving an adequate statement about the processing properties of granulated material to be added to unvulcanized rubber a testing device is used consisting of a support for the test sample, a wedge-shaped tool and a linearly acting pressure generator, whereby as support, bearing means for agglomerates are arranged on either side of the working plane of the movable wedge-shaped tool with bearing forces acting predominantly parallel thereto.

10 Claims, 4 Drawing Sheets

TESTING DEVICE FOR DETERMINING MECHANICAL PROPERTIES OF A GRANULATED MATERIAL

The invention relates to a testing device for determining mechanical properties, in particular the tensile strength, when mixing a granulated material into unvulcanized rubber, consisting of a support for the test sample, a wedge-shaped tool and a linearly acting pressure generator.

Various additives are mixed into a crude rubber before vulcanization. The vulcanization behaviour can thus be controlled and the physical properties of the finished rubber article and the ageing resistance thereof can thus be improved.

These additives were formerly added to the rubber exclusively in the form of fine-grained powders. For reasons of hygiene in work and to improve the ease of addition, agglomerated additives (granulated materials) have for some time been used on an increased scale.

This granulated material has defined properties with respect to porosity, hardness, tensile strength and dispersability during incorporation into the rubber, depending on the make-up of the substance and method of processing. With regard to the quality of the finished rubber articles, in particular of commercial articles such as car tyres, it is of decisive importance for the granulated material to be broken down as finely as possible during incorporation so as to avhieve optimum utilization in the rubber and to prevent destruction of the rubber under load owing to initial tears as the result of excessively large particles. Two conflicting properties are thus required. A solid agglomerate is required for handling purposes and it is then broken down easily and completely again into the grains making up the granulated material during incorporation into the crude rubber.

It is known that granulated material can be mixed into a rubber and that it is then possible to determine by sight tests whether the granulated material has been broken down finely again.

However, the test is inaccurate because it is very difficult perfectly to determine the finest fractions. The test is also very expensive, so it is not particularly suitable for production control.

An object of the invention is to find a testing device which allows an adequate statement about the processing properties with reference to parameters (shearing force, tensile strength) to be made in a short period (10 to 20 minutes) before the agglomerated additive (granulated material) has been incorporated into an unvulcanised rubber.

The object is achieved according to the invention in that, as support, bearing surfaces for agglomerates are arranged on either side of the working plane of the movable flat wedge-shaped tool with bearing forces acting predominantly parallel thereto.

It is surprising that sufficiently precise parameters for determining dispersability when adding these additives to the rubber can be determined by splitting the small granules.

When placed onto the agglomerate, in particular granules, the wedge-shaped tool actually forms a wedge of material which is triangular in cross-section in the upper region of contact which wedge, during further loading, causes the cross-section located thereunder to spring apart under further load so that tensile stresses are created perpendicularly to the subsequent splitting face. The path of forces is recorded during this process. Conclusions about the incorporability of the additive in the rubber can be drawn from this when the rubber is subsequently used as a granule in a calendar.

The splitting of an individual granule or pellet requires only a very short time so a large number of samples can be tested in an acceptable time of 10 to 30 minutes so that a statement about the incorporability can be made by using a statistic mean value even if the shapes now exisiting during production of a granule are not exact.

With the cylindrical granule normally used, the straight cutting edge of the wedge initially contacts the granulated material only in the centre and then makes up the wedge of material from the inside outwards, preventing premature lateral eruptions. Furthermore, the lower linear bearing means, transverse to the working plane of the wedge does not prevent the splitting process because the granulated material can move freely in the direction of the longitudinal axis so a lower undesirable wedge of material is barely formed. This procedure is assisted if a respective linear bearing means is arranged, for example, on each side of the vertical central plane of the lying cylindrical granulated material.

It is advantageous to use a feed device which can comprise a linearly movable or rotatable magazine, which magazine simultaneously orientates the granules and acts as a bearing means during the splitting process or merely adds the granules to the bearing means serving for the splitting process.

By arranging a counter-wedge-shaped tool which is movable in the opposite direction in the working plane of the wedge-shaped tool, it is possible to charge the sample symmetrically so that the shear zones which are almost symmetrical on both sides pass into the tensile region.

It has been found advantageous to round the wedge-shaped tool at the front so as to be able to form a suitably large wedge of material even with a more flexible granulated material. Granules having a diameter D of from 1 to 4 mm, in particular of from 1.5 to 2.5 mm are preferably used during the tests with cylindrical extruded rubber additives. The radii R of the wedge-shaped tool are from 0.1 to 0.4 mm. The quotient $R/D$ should lie between 0.05 and 0.2, in particular between 0.075 to 0.125.

Automatic centering is carried out by a joint between, for example, a wedge-shaped tool and a connecting rod of the hydraulic cylinder as pressure generator, so that a similar wedge of material is made up, even in the case of slight unevenness, increasing the accuracy of measurement.

Finally, hard positioning onto the granules can be avoided by an elastic, dampened intermediate member between pressure generator and wedge-shaped tool. The material thus has sufficient time to form the wedge of material before the actual splitting process begins.

The linear supporting bearing means extended transversely to and on either side of the working plane of the wedge-shaped tool, rectangular or V-shaped cross-sections or other polygonal boundaries having proven to be particularly desirable.

If the feed rate can be varied continuously or in steps, it is possible to reduce the non-productive time (for example return). On the other hand, it is important to give the material sufficient time, owing to its inertia, to be able to form the wedge of material cleanly so that further testing of the tensile stress can be carried out at a high feed rate.

All granules with cylindrical, elliptical, polygonal and spherical cross-sections are suitable as test sample.

An example of the testing device is shown in the drawings and is described below.

FIG. 1 shows a testing device 1 in which a supported frame 2 bears the individual components.

Figure 1:
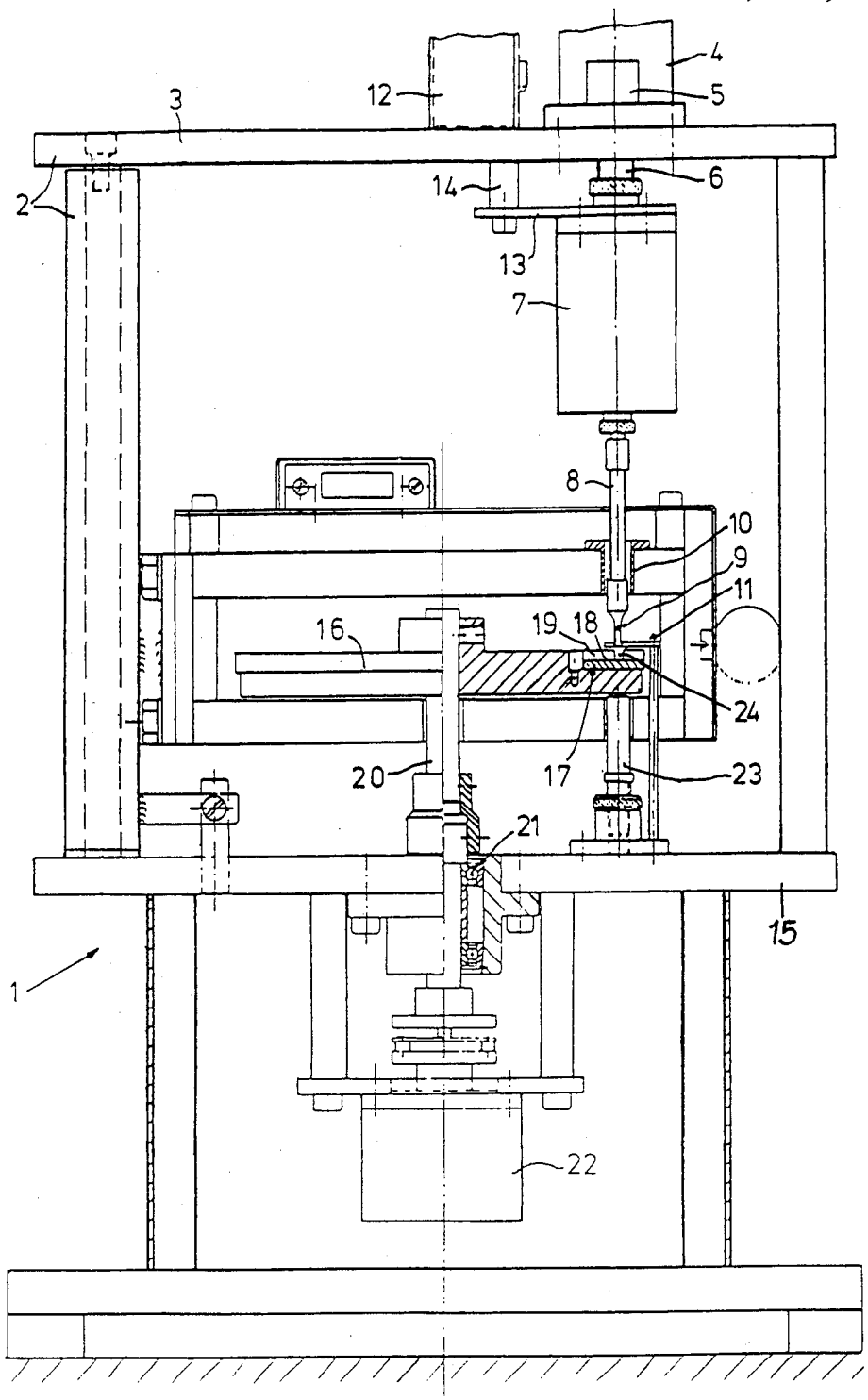
FIG. 1 shows a side view of the testing device.

Above the upper bar 3 there is arranged a pressure generator 4 which is composed of an adjustable motor 5 and a spindle 6 connected in turn via a force pick-up 7 and a conecting rod 8 to the exchangeable wedge-shaped tool 9. This wedge-shaped tool 9 is guided through a sliding bearing 10 in the upper region and is surrounded by a stripper 11 in the lower region.

A potentiometer 12 which is connected to the force pick-up 7 via a lever 13 and a rod 14, is also arranged on the upper bar 3.

A turntable is arranged on the lower bar 15 as feed device 16 and has radially orientated grooves 18 with parallel bearing means 19 on its outer circle 17. The turntable 16 can be rotated in step-wise manner in ball bearings 21 round the central axis 20 by a two-phase motor 22.

A lifting ram 23 can also act as a support in the region of the circle 17.

Figure 2:
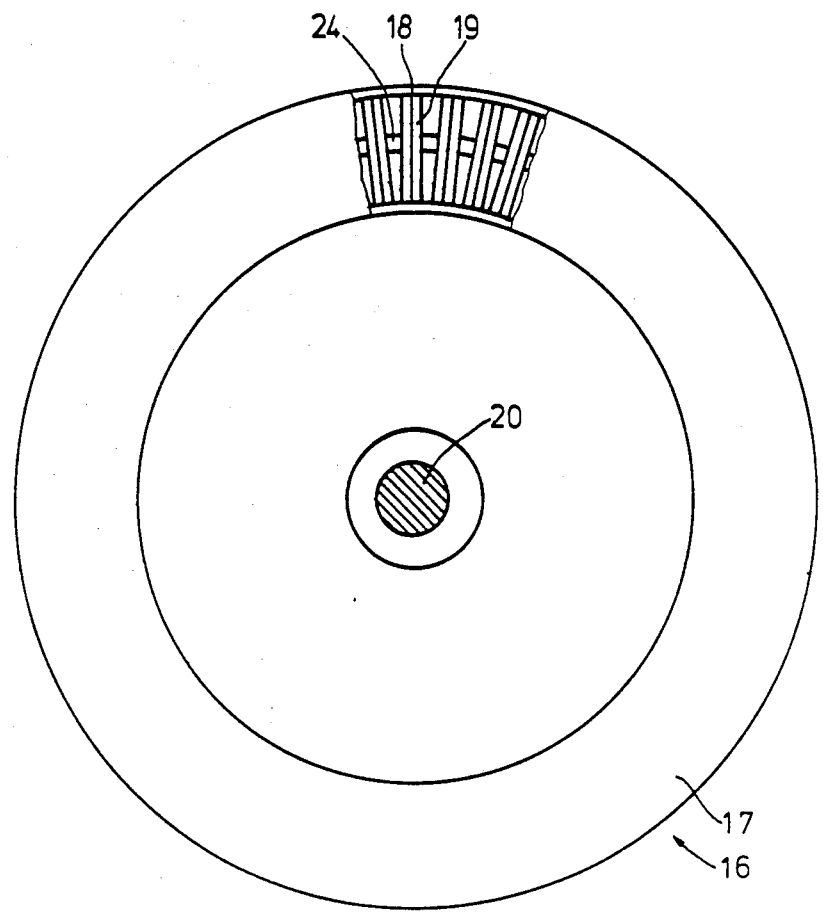
FIG. 2 shows plates for granules

FIG. 2 shows a turntable 16 in which rectangular grooves 18 with a base and parallel vertical walls 19 are arranged on an outer ring 17 for fixing the cylindrical granules, a free circumferentially running gap 24 for the at least partial immersion of the wedge-shaped tool 9 being provided in the center of the groove.

Figure 3:
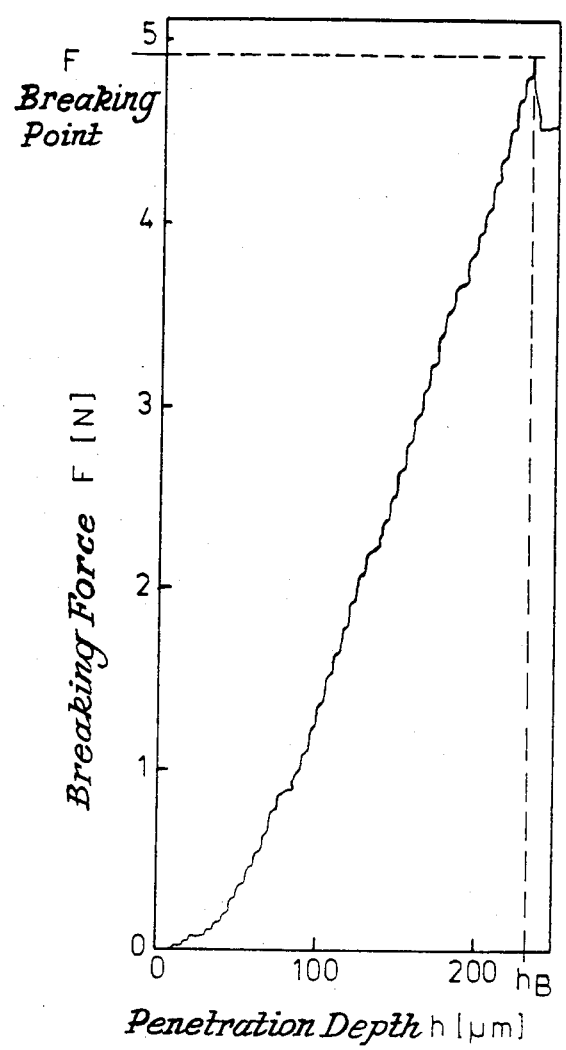
FIG. 3 is a curve graph showing breaking force/depth.

FIG. 3 shows a graph concerning the force/path. With a slight increase in force, the curve firstly runs very flat for forming the wedge of material and then rises almost proportionally up to the breaking load.

Figure 4:
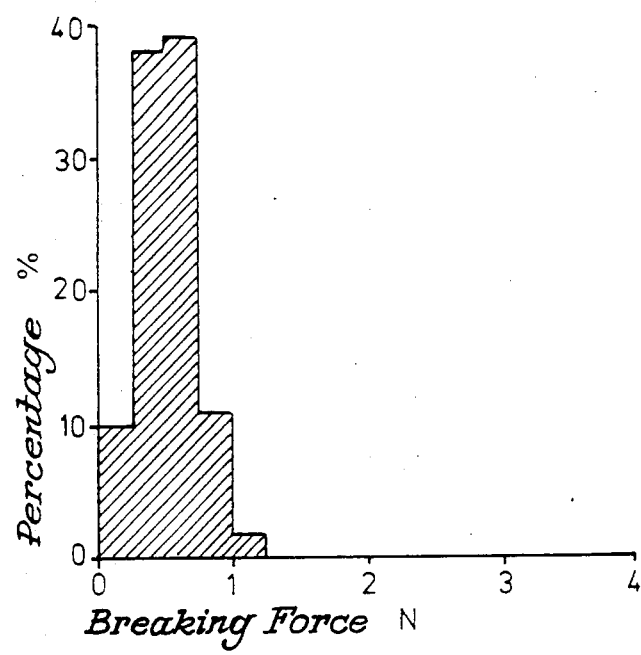
FIG. 4 is a histogram with slight scattering.
Figure 5:
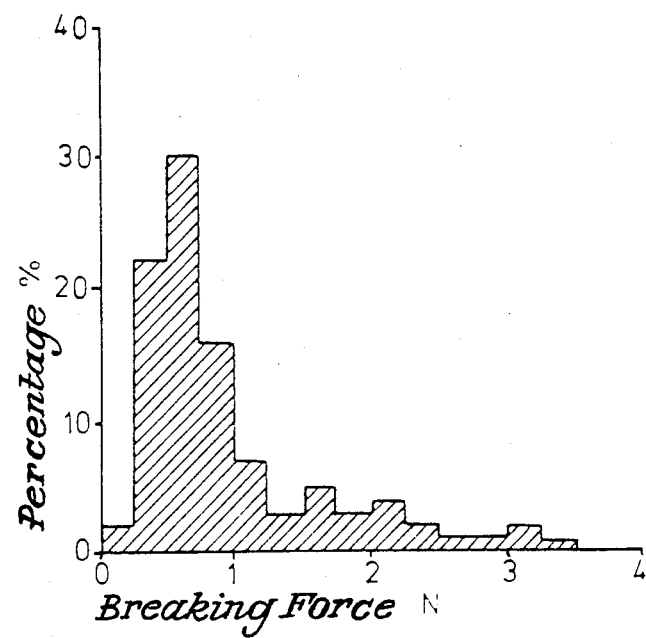
FIG. 5 is a histogram with broad scattering.

FIGS. 4 and 5 shows histograms of the measured breaking forces of 100 respective cylindrical granules which have been agglomerated by roller granulation or by extrusion. FIG. 4 has a narrow frequency distribution with low maximum breaking forces so this granulated material will disperse readily when incorporated whereas FIG. 5 has a widely scattered frequency distribution with high mean value of the breaking force. This test result implies poor incorporability of the granulated material into the rubber.

The process took place in the following stages:

The ram is lowered towards the granulated material to a distance of 0.5 mm from it at high spped (1 mm/min). Then the ram is further lowered slowly at constant speed until the wedge of material is formed in the granulated material and the granulated material breaks. The peak force value occurring is stored. The lowering speed of the wedge-shaped tool lies in the range of from 1 to 10 mm/min. Conclusions about the structure of the granules and the dispersability thereof into the rubber can be drawn from the recorded force curve. The ram is quickly raised after breakage. The granulated material adhering to the wedge-shaped tool in some cases is prevented from rising by a stripper and falls back onto the plate. The next measurement can be taken after positioning the next granulated material by further rotation of the plate.

We claim:

1. A testing device for determining mechanical properties, such as tensile strength, of granulated material to be mixed into unvulcanized rubber, the testing device comprising a support for a granule as a test sample and a wedge-shaped tool, the support having a form in the shape of a groove having a longitudinal axis and constructed and arranged to bear the granule, the wedge-shaped tool being arranged above the groove with its wedge end transverse to the longitudinal axis of the groove, and a linearly acting pressure generator connected to move the wedge-shaped tool toward and away from the groove.

2. A tesing device as in claim 1 including a rotatable horizontally oriented magazine for granules, the magazine having a plurality of radially orientated grooves.

3. A testing device as in claim 1 iucluding a counter-pressure tool arranged below the support, and a pressure generator connected to move the counter-pressure tool toward and away from the groove.

4. A testing device as in claim 1 wherein the wedge end of the wedge-shaped tool has a radius of from 0.2 to 0.4 mm.

5. A testing device as in claim 1, wherein the wedge end of the wedge-shaped tool has a radius of from 0.15 to 0.25 mm.

6. A testing device as in claim 1 wherein the wedge-shaped tool is pivotally mounted.

7. A testing device as in claim 1 including an elastic and thermally insulating intermediate member between the pressure generator and wedge-shaped tool.

8. A testing device as in claim 1 wherein the pressure generator has a variable feed rate.

9. A testing device as in claim 1 wherein the groove has a V-shaped, rectangular or other polygonal cross-section.

10. A testing device as in claim 1 wherein the groove includes a transverse groove constructed and arranged to receive the wedge end of the wedge-shaped tool.

* * * * *